Figure 1:
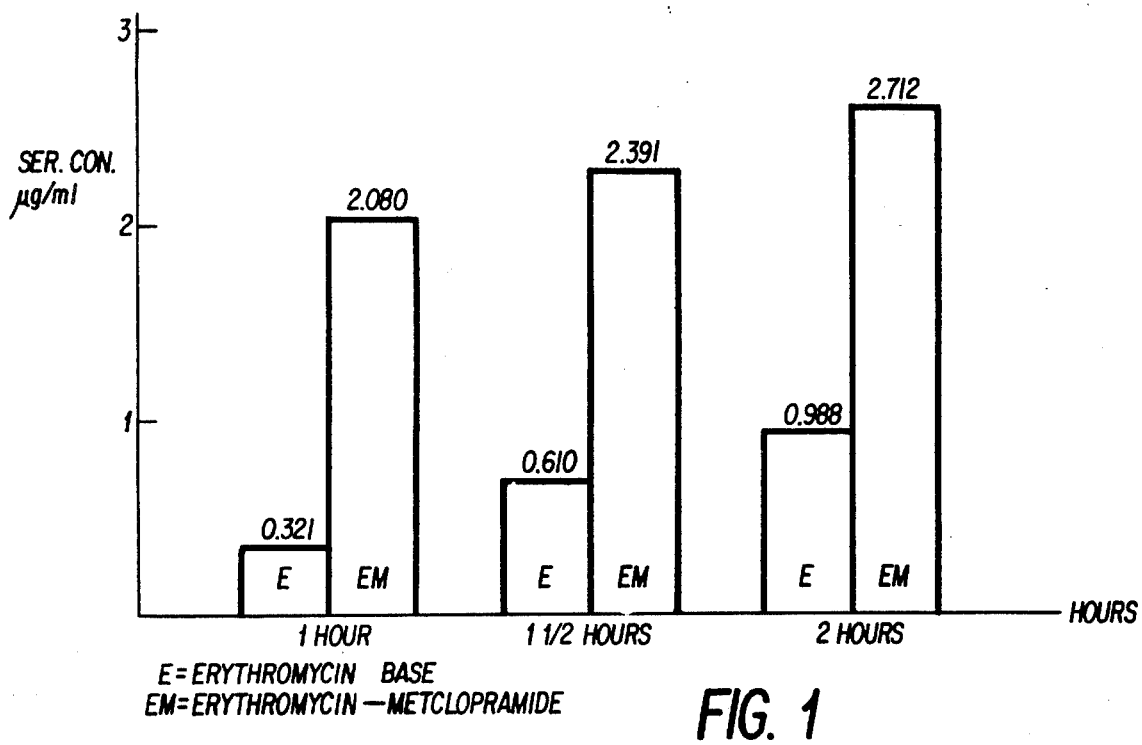

United States Patent [19]
Barbier

[11] 4,176,180
[45] Nov. 27, 1979

[54] PHARMACEUTICAL COMPOSITION COMPRISING ERYTHROMYCIN AND METOCLOPRAMIDE AND METHOD OF PREPARING SAME

[75] Inventor: Pierre Barbier, Paris, France

[73] Assignee: Societe d'Etudes Scientifiques et Industrielles, Paris, France

[21] Appl. No.: 911,611

[22] Filed: Jun. 1, 1978

[30] Foreign Application Priority Data

Jun. 3, 1977 [GB] United Kingdom ............... 23727/77

[51] Int. Cl.² .................... A61K 31/71; A61K 31/165
[52] U.S. Cl. ..................................... 424/181; 424/324
[58] Field of Search ................................. 424/181, 324

[56] References Cited
PUBLICATIONS

Chemical Abstracts, 78:67149j (1973).
The Merck Index, 8 Ed., 1968, Merck & Co., Inc., Rahway, N. J., p. 419.

Primary Examiner—Jerome D. Goldberg
Attorney, Agent, or Firm—John C. Smith, Jr.

[57] ABSTRACT

A pharmaceutical composition comprising erythromycin and metoclopramide or a therapeutically acceptable salt thereof. The antibiotic activity of the erythromycin when administered to a patient has been found to be substantially improved by the presence of the metoclopramide or the therapeutically acceptable salt thereof.

6 Claims, 2 Drawing Figures

PHARMACEUTICAL COMPOSITION COMPRISING ERYTHROMYCIN AND METOCLOPRAMIDE AND METHOD OF PREPARING SAME

The present invention is concerned with a novel pharmaceutical composition comprising as active substances erythromycin, an antibiotic belonging to the macrolide family, and N-(2-diethylaminoethyl)-2-methoxy-4-amino-5-chlorobenzamide, hereinafter referred to as metoclopramide, or a pharmaceutically acceptable salt thereof. Metoclopramide and its salts are known for their effect on the digestive process as an antiemetic and are described in U.S. Pat. No. 3,177,252 to Thominet which is incorporated by reference. The composition of the present invention may further include inert non-toxic substances or carriers normally used in pharmaceutical compositions.

Although the efficiency of erythromycin as an antibiotic is comparable to that of penicillin, its antibacterial spectrum actually being wider than that of penicillin, and although erythromycin has the least side effects of the antibiotics currently used, erythromycin is not the most widely used antibiotic. This is probably due to the fact that erythromycin is partially inactivated by gastric acidity. Efforts have been made to overcome this disadvantage by administering the antibiotic in the form of coated compressed tablets or in the form of more resistant salts or esters. However, assimilation of these preparations in the intestine varies resulting in irregular concentrations of the antibiotic in the blood stream. Furthermore, some esters have adverse side effects. For example, the lauryl sulfate of the propionic ester of erythromycin, identified as estolate, has the disadvantage that in some patients it causes not inconsiderable hepatotoxicity after prolonged treatment.

It has been surprisingly discovered that when administering the pharmaceutical composition of the present invention in which the integrity of the erythromycin base molecule is preserved, as it is simply associated with metoclopramide, serum concentrations of erythromycin are attained which have normal activity, the minimum effective serum concentration (CME) of erythromycin, for therapeutic purposes, being on the order of 1 µq/ml of serum.

Figure 2:
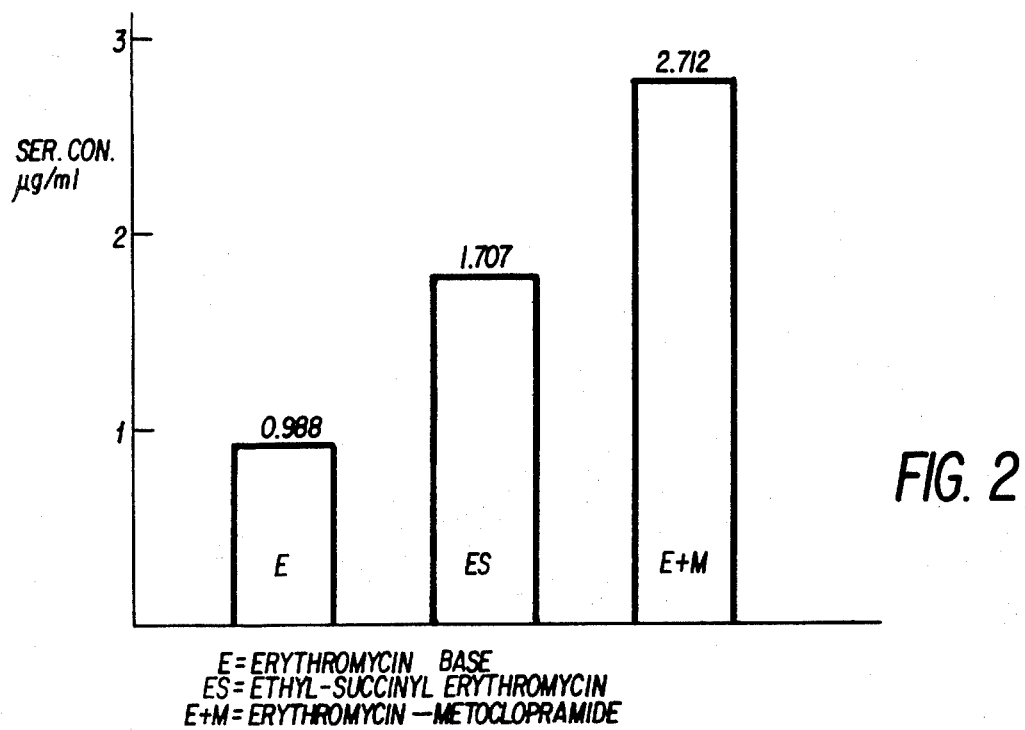

The invention will now be described with reference to the accompanying drawings in which:

FIG. 1 is a graph comparing the results obtained by administration to a patient of erythromycin alone and of the pharmaceutical composition of the present invention, and FIG. 2 is a graph comparing the results obtained by administration to a patient of erythromycin alone, of an erythromycin ester and of the pharmaceutical composition of the present invention.

The following example compares the serum concentrations of erythromycin administered alone and administered with metoclopramide and demonstrates the substantially improved serum concentrations of erythromycin obtained in accordance with the present invention.

EXAMPLE 1.

Twenty persons were subject to a double experiment wherein each person received 600 mg of pure erythromycin (E) in a single dose and three days later received a single dose of 600 mg of erythromycin and 10 mg of metoclopramide dihydrochloride (E+M). The serum concentrations of erythromycin were evaluated on several occasions during this period for the purpose of detecting the maximum serum concentration governing therapeutic activity. The results are set forth in the following table:

TABLE I

| | Serum concentration of erythromycine expressed as (µg/ml of serum) | | | | | |
|---|---|---|---|---|---|---|
| | 1 hour following administration | | 1½ hours following administration | | 2 hours following administration | |
| | E | E+M | E | E+M | E | E+M |
| 1 | 0.35 | 1.15 | 1.3 | 3.1 | 1.25 | 2.3 |
| 2 | 0 | 0.23 | 0 | 0.35 | 0.45 | 0.64 |
| 3 | 0 | 0 | 0 | <0.1 | 0 | 1.4 |
| 4 | 0 | 2.6 | 3.3 | 3.2 | 3.9 | 4.8 |
| 5 | 0 | 4.3 | 0 | 4.7 | 0 | 4.4 |
| 6 | 0 | <0.1 | <0.1 | 0.6 | 0.12 | 1.55 |
| 7 | 0 | 0.5 | 0 | 4.5 | <0.1 | 4.4 |
| 8 | <0.1 | 3.9 | <0.1 | 3.6 | 1.35 | 2.9 |
| 9 | 0.14 | 3.6 | 0.98 | 3.6 | 1.2 | 3.6 |
| 10 | 0 | 0.31 | 0 | 1.3 | 0.13 | 0.86 |
| 11 | 0.24 | 0 | 0.27 | 0.23 | 0.64 | 2.8 |
| 12 | 0 | 0 | 0.16 | 1 | 1.05 | 3.4 |
| 13 | 0.9 | 6.8 | 1 | 3.4 | 1.75 | 2.6 |
| 14 | 0 | 1.4 | 0 | 2.5 | 0.1 | 3.3 |
| 15 | 0 | 0 | 0 | <0.1 | <0.1 | 0.14 |
| 16 | <0.1 | 0.21 | 0.1 | 3.2 | 1.35 | 1.95 |
| 17 | <0.1 | 4.5 | <0.1 | 1.95 | <0.1 | 3 |
| 18 | <0.1 | 2.3 | <0.1 | 2.4 | 0.58 | 2.6 |
| 19 | 4.4 | 6.8 | 4.6 | 5.4 | 4.5 | 5 |
| 20 | 0 | 2.9 | <0.1 | 2.6 | 1.1 | 2.6 |
| Total | 6.43 | 41.6 | 12.21 | 47.83 | 19.77 | 54.24 |
| Average | 0.321 | 2.08 | 0.610 | 2.391 | 0.988 | 2.712 |

(Values of less than 0.1 were taken as 0.1.)

The maximum observed serum concentrations, based upon the major data with respect to antibiotic therapy, are compared and summarized in the following table.

TABLE II

| | Maximum concentrations of erythromycin (µg/ml of serum) | |
|---|---|---|
| | E max | (E + M) max |
| 1 | 1.30 | 3.10 |
| 2 | 0.45 | 0.64 |
| 3 | 0 | 1.40 |
| 4 | 3.90 | 4.80 |
| 5 | 0 | 4.70 |
| 6 | 0.12 | 1.55 |
| 7 | 0.10 | 4.50 |
| 8 | 1.35 | 3.90 |
| 9 | 1.20 | 3.60 |
| 10 | 0.13 | 1.30 |
| 11 | 0.64 | 2.80 |
| 12 | 1.05 | 3.40 |
| 13 | 1.75 | 6.80 |
| 14 | 0.10 | 3.30 |
| 15 | 0.10 | 0.14 |
| 16 | 1.35 | 3.20 |
| 17 | 0.10 | 4.50 |
| 18 | 0.58 | 2.60 |
| 19 | 4.60 | 6.80 |
| 20 | 1.10 | 2.90 |
| Total | 19.92 | 65.93 |
| Average m | 0.996 | 3.296 |

$$p = \frac{m\,(E + M)\,max}{m\,E\,max} = 3.31$$

It was found that on average the minimum effective serum concentration (CME) is not achieved with erythromycin alone (average achieved: 0.996 µg/ml) whereas with the pharmaceutical composition of the present invention the serum concentrations obtained very largely exceed on average the CME (average attained: 3.296 μg/ml) and are more than three times greater than those achieved with erythromycin alone. Thus, the pharmaceutical composition of the present invention makes it possible to obtain reliable antibiotic activity which is greater than that of erythromycin alone.

Statistical analysis of the results were carried out by comparing averages relating to the differences (in this case the increase) in the maximum serum proportions of erythromycin after administration of erythromycin alone and after administration of the erythromycin-metoclopramide composition. The results are summarized in the following table:

TABLE III

| Maximum serum concentrations of erythromycin in μg/ml | |
|---|---|
| m | 2.3005 |
| S | 1.455 |
| t | 7.7071 |
| P | <0.001 | m = average of the differences in maximum serum concentrations between (E + M) and (E).
t = variable in accordance with the Student law.
P = probability that the theoretical distribution average M is: $0 < M > 2m$.

Thus, with a 99.9% probability, the difference in maximum serum concentrations between the pharmaceutical composition of the present invention and erythromycin alone is on average positive and represents a highly significant increase.

In addition, whereas the serum concentration of erythromycin is low and varies substantially from one patient to another in the case of the administration of erythromycin alone, the serum concentration in the case of the administration of the pharmaceutical composition of the present invention, becomes markedly higher as shown by the graph of FIG. 1 and also becomes more regular as shown in Table II. These results show clearly the superiority of the pharmaceutical composition of the present invention over erythromycin alone.

A comparison was made between the results observed with the pharmaceutical composition of the present invention and those observed with an erythromycin ester such as ethyl-succinyl erythromycin, an antibiotic in current use. A 600 mg dose (three 200 mg compressed tablets) of ethyl-succinyl erythromycin (ES) was administered to each of nine ill persons, and the serum concentrations of erythromycin were evaluated two hours following administration. The results are set forth in the following table:

TABLE IV

| Serum concentration of erythromycin two hours following administration of 600 mg of ethyl-succinyl erythromycin (μg/ml of serum). | |
|---|---|
| Obs | Erythromycin (ES) |
| 1 | 3.20 |
| 2 | 2.40 |
| 3 | 0.29 |
| 4 | 2.70 |
| 5 | 0.56 |
| 6 | 4.70 |
| 7 | 0.74 |
| 8 | 0.62 |
| 9 | 0.15 |
| Total | 15.36 |
| Average | 1.707 |

It was found that, as with erythromycin alone, there is an irregularity in the serum concentrations obtained. Even the average serum concentration observed with the ester (1.707 μg/ml) is higher than that of the erythromycin alone (0.988 μg/ml), it nonetheless is substantially lower than that of the pharmaceutical composition according to the present invention (2.712 μg/ml) as shown in FIG. 2.

The novel pharmaceutical composition according to the present invention is suitable for the treatment of bacterial diseases involving bacteria which are susceptible to erythromycin (see Table V) and in particular infections or secondary infections of the respiratory tract and the ENT sphere and in the prophylaxis of post-operational infection.

TABLE V

| MINIMUM INHIBITING CONCENTRATIONS OF ERYTHROMYCIN (MICROGRAMS PER MILILITER OF MEDIUM) | |
|---|---|
| GRAM POSITIVE COCCI | |
| Diplococcus pneumoniae | 0.01–0.2 |
| Str. pyogenes | 0.02–0.2 |
| Str. non-groupable | 0.02–3.1 |
| Str. faecalis | 0.6–3.1 |
| Staph. aureus | 0.01–1.6 |
| Staph. epidermidis | 0.2–3.1 |
| GRAM NEGATIVE COCCI | |
| Neisseria menigitidis | 0.2–1.6 |
| Neisseria gonorrhoeae | 0.04–0.4 |
| GRAM POSITIVE BACILLI | |
| Corynebacterium diphteriae | 0.2–3.1 |
| Listeria monocytogenes | 0.2 |
| Erysipelothrix insidiosa | 0.06 |
| Plectridium tetani | 0.2–0.6 |
| Clostridium perfringens | 0.1–0.2 |
| GRAM NEGATIVE BACILLI | |
| Haemophilus influenzae | 0.4–3.1 |
| Bordetella pertussis | 0.2 |
| Pasteurella multocida | 0.8 |
| Brucella melitensis | 0.3 |
| Bacteroides fragilis | 0.8–6.2 |
| MYCOPLASMAE | |
| Mycoplasma pneumoniae | 0.004–0.016 |

The pharmaceutical composition according to the present invention may be prepared by mixing erythromycin with metoclopramide or one of its pharmaceutically acceptable salts and optionally with the usual pharmaceutically acceptable non-toxic excipients or vehicles.

The pharmaceutical composition of the present invention may be used in the form of capsules, compressed tablets, sugar-coated pills, powder, granules and drinkable suspensions. Conventional methods for preparing these different forms may be used. Additional substances which do not react with the erythromycin and metoclopramide may be added, as for example, lactose, magnesium stearate, starch, talcum, celluloses, levilite, Tween 80 (a complex mixture of polyoxyethylene ethers of mixed partial oleic esters of sorbitol anhydrides), saccharose and other vehicles which are employed in medicinal preparations.

The weight ratio of the two compounds, erythromycin and metoclopramide, may vary within wide limits. About 10 to 200 parts by weight and preferably 20 to 100 parts by weight of erythromycin are advantageously used with 1 part by weight of metoclopramide or the equivalent amount, stated in the form of the metoclopramide base, of one of its pharmaceutically acceptable salts.

The preferred adult dosage, which may be divided into two doses per day, is from 5 to 10 mg of metoclopramide, or the equivalent amount, stated in the amount of the metoclopramide base, of one of its pharmaceutically acceptable salts, with 400 to 600 mg of erythromycin.

The preferred pediatric form comprises a suspension of the two micro-encapsulated active substances, the daily dosage per kilo being from 0.25 to 0.50 mg of metoclopramide, or the equivalent amount, stated in the form of the metoclopramide base, of one of its pharmaceutically acceptable salts, with 30 to 50 mg of erythromycin.

EXAMPLE 2.

Compressed tablets were prepared having the following composition:

| Erythromycin base | 0.300 g |
|---|---|
| Metoclopramide monohydrochloride (expressed in base form) | 0.005 g |
| Dried Fecula | 0.065 g |
| Lactose | 0.150 g |
| Methylcellulose 1500 cps | 0.0065 g |
| Levilite | 0.021 g |
| Magnesium stearate | 0.009 g |

To prepare the tablets, erythromycin and metoclopramide were mixed with the dried fecula and the lactose in a process comprising successive dilution steps. The mixture was granulated with methylcellulose. Levilite and magnesium stearate were added to the granulated material before being compressed into tablets.

Other suitable granulating agents include ethyl cellulose, polyvinylpyrrolidone, fecula paste, gum arabic, etc. Disintegrating agents other than fecula which may be used include maiz starch, carboxymethylfecula, alginate, microcrystalline cellulose, etc.

EXAMPLE 3.

Granulated pellets having the following composition were prepared:

| Erythromycin base | 0.600 g |
|---|---|
| Metoclopramide monohydrochloride (expressed in base form) | 0.010 g |
| Monocrystalline cellulose (Avicel RC 591) | 0.200 g |
| Saccharinate | 0.020 g |
| Carboxymethylcellulose 7 HOXF | 0.200 g |
| Tween 80 | 0.003 g |
| Aroma in powder form | s.q. |
| Saccharose | s.q. for 5 g |

To prepare the granulated pellets, erythromycin and metoclopramide were mixed with saccharinate, Tween 80 and saccharose. The mixture was granulated with carboxymethylcellulose. After granulation and drying, the monocrystalline cellulose and the scent were added.

The monocrystalline cellulose may be replaced with veegum or any other thickening agent.

EXAMPLE 4.

A powder having the following composition was prepared, the powder being used to form a suspension.

| Erythromycin base | 3 g |
|---|---|
| Metoclopramide monohydrochloride (expressed in base form) | 0.050 g |
| Monocrystalline cellulose | |
| (Avicel RC 591) | 0.800 g |
| Saccharinate | 0.100 g |
| Carboxymethylcellulose 7 HOXF | 0.800 g |
| Tween 80 | 0.030 g |
| Aroma in powder form | s.q. |
| Saccharose | s.q. for 50 g |

After crushing, the components were mixed. 50 g of the mixture was then added to 150 ml of water to form a solution which may be kept in a refrigerator. One soupspoonfull contains 300 mg of erythromycin and 5 mg of metoclopramide (expressed in base form).

The saccharose may be replaced by a mixture of saccharose/mannitol.

The following examples demonstrate the effectiveness of the pharmaceutical composition of the present invention in the treatment of humans:

EXAMPLE 5.

A dose of the phamaceutical composition of the present invention comprising 600 mg of erythromycin and 10 mg of metoclopramide was administered each morning and evening to a 37 year old patient suffering from angina of type $\beta$ haemolytic streptococcus (Group A—positive sample) and having a fever of 40° C. with intense dysphagia.

There was rapid defervescence and complete absence of fever in 48 hours. Treatment was continued for 10 days and throat samples taken on the 14th and 21st days were negative. Tolerance was perfect with no observed secondary effect. Urine samples were normal.

EXAMPLE 6.

A dose of the pharmaceutical composition of the present invention comprising 600 mg of erythromycin and 10 mg of metoclopramide was administered each morning and evening to a 51 year old patient, a heavy smoker, suffering from attacks of repetitive chronic bronchitis secondary infection. There was total defervescence with complete drying of expectoration in four days. Tolerance was perfect with no secondary effects observed.

I claim:

1. A pharmaceutical composition comprising 60 parts by weight of erythromycin and one part by weight of metoclopramide or the equivalent amount, in the form of the base, of a therapeutically acceptable salt thereof.

2. A pharmaceutical composition according to claim 1 further comprising an inert non-toxic substance or vehicle.

3. A pharmaceutical composition according to any one of claims 1 and 2 wherein said metoclopramide is in the base form.

4. A pharmaceutical composition according to any one of claims 1 and 2 wherein said metoclopramide is in its form of a monohydrochloride.

5. A pharmaceutical composition according to any one of claims 1 and 2 wherein said metoclopramide is in the form of a dihydrochloride.

6. A method of suppressing inactivation of erythromycin by gastric acidity and increasing the total amount of erthromycin absorbed in a human following oral administration of erythromycin to said human, said method comprising orally administering an effective amount of a pharmaceutical composition comprising 60 parts by weight of erythromycin per part by weight of metoclopramide or the equivalent amount, in the form of the base, of a therapeutically acceptable salt thereof.

* * * * *